United States Patent [19]

Lesser et al.

[11] 4,087,490

[45] May 2, 1978

[54] CYCLIC PHOSPHORYL AND THIOPHOSPHORYL HALIDES

[75] Inventors: Joseph Herman Lesser; Ludmila Friedman, both of Beer-Sheva, Israel

[73] Assignee: Makhteshim Chemical Works, Ltd., Beer-Sheva, Israel

[21] Appl. No.: 707,093

[22] Filed: Jul. 20, 1976

[30] Foreign Application Priority Data

Jul. 31, 1975 Israel .......................................... 47851
Jul. 31, 1975 Israel .......................................... 47852

[51] Int. Cl.² ............................................... C07F 9/15
[52] U.S. Cl. ................................... 260/974; 260/937; 260/975
[58] Field of Search ............................... 260/974, 937

[56] References Cited

U.S. PATENT DOCUMENTS

| 3,159,664 | 12/1964 | Bartlett | 260/974 X |
| 3,235,448 | 2/1966 | Oshima et al. | 260/937 X |
| 3,478,133 | 11/1969 | Oshima et al. | 260/937 |
| 3,978,167 | 8/1976 | Albright | 260/937 X |

*Primary Examiner*—Anton H. Sutto
*Attorney, Agent, or Firm*—Browdy and Neimark

[57] ABSTRACT

Compounds of the formula

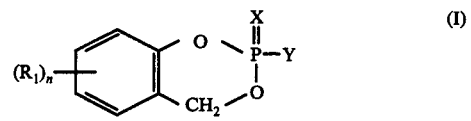

wherein $R_1$ is selected from the group consisting of hydrogen, alkyl, alkenyl, cycloalkyl, aryl, alkaryl, aralkyl, halogen, cyano, nitro, alkoxy, alkylthio, aryloxy, haloalkyl, and haloaryl, $n$ is 0, 1, 2, 3 or 4; X is oxygen or sulfur, Y is chlorine or bromine and a process for the production of these; and for the conversion of these to valuable insecticides by reacting same with an alkanol.

6 Claims, No Drawings

CYCLIC PHOSPHORYL AND THIOPHOSPHORYL HALIDES

FIELD OF THE INVENTION

The invention relates to novel 2-halo-4H-1,3,2-benzodioxaphosphorin-2-oxides and 2-oxides and 2-sulfides, to a process for the production of these and for the conversion of same by reaction with a suitable alkanol to active insecticides of the 2-alkoxy-4H-1,3,2-benzodioxaphosphorin-2-oxide and 2-sulfide type.

BACKGROUND OF THE INVENTION

Cyclic halo-phosphate and thiophosphate esters, commonly known as phospholanes are well known in the literature, as, for example, British Pat. No. 766,766. These compounds have been prepared by reacting 1,2- or 1,3- glycols with a phosphoryl or thiophosphoryl trihalide in the presence of a tertiary base such as pyridine. Aromatic cyclic halo-phosphate and thiophosphate esters have also been known for a long time. See, for example, L. Anschuetz and W. Broeker, Ber., 61B (1928) 1264 (C.A., 22: 4113).

Benzylic cyclic halo-phosphate and thiophosphate esters, have, however, not been disclosed in the literature. This is surprising particularly since o-benzylic cyclic phosphate and thiophosphate triesters have been reported recently as being useful insecticides. See Belgian Pat. 633,481 (C.A., 61: 9541a) and the publications of M. Eto and co-workers [Agr. Biol. Chem., 29(1965)243; 30(1966) 181 (C.A., 64; 17627f)]. These latter compounds were invariably prepared by reacting an o-hydroxybenzyl alcohol with an alkoxy phosphoryl or thiophosphoryl dihalide in the presence of a base such as pyridine or other tertiary amine.

Our experiments have shown that the standard procedures used to prepare cyclic halo-phosphate and thiophosphate esters cannot be used to prepare the benzylic analogues. Reaction of an o-hydroxy-benzyl alcohol with a phosphoryl or thiophosphoryl trihalide in the presence of a tertiary base was found to yield polymeric tars. Cyclic phosphorus-containing esters having the general formula (II)

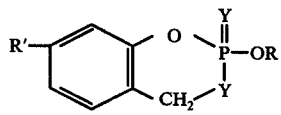

wherein R is an alkyl radical, R' is a hydrogen atom or an alkyl radical, X is oxygen or sulfur, and Y is an oxygen or an N-aryl-radical, have been known to possess significant insecticidal activity (British Pat. No. 987,378).

These compounds have been prepared by reacting for example, O-hydroxy-benzyl alcohol or its derivatives with either alkoxyphosphoryl dichloride or alkoxy thiophosphoryl dichloride in a solvent in the presence of a dehydrochlorinating agent, for example, a tertiary base such as pyridine or triethylamine.

More recently, an improved process was disclosed (Japanese Pat. No. 7,028,183) whereby the reaction is conducted in an aqueous alkaline hydroxide medium to give a much higher yield.

All of the previous processes, however, are based on the use of alkoxy phosphoryl or thiophosphoryl dichloride as one of the reactants. These, however, are unstable liquids, having a very short shelf life. Furthermore, they are difficult to prepare particularly in a pure form and the cyclic phosphorous esters prepared from thiophosphoryl dichloride are vile smelling due to impurities in the reaction product which are not readily removed.

SUMMARY OF THE PRESENT INVENTION

The present invention relates to novel compounds of the formula

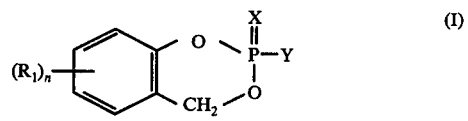

wherein $R_1$ is selected from the group consisting of hydrogen, alkyl, alkenyl, cycloalkyl, aryl, aralkyl, alkaryl, alkoxy, halogen, cyano, nitro, alkylthio, aryloxy, haloalkyl, and haloaryl, n is 0,1,2,3 or 4; X is oxygen or sulfur and Y is chlorine or bromine, and to a process for the production of these. The process of the present invention is characterized in that the novel compounds can be prepared in high yield and quality. The novel compounds of the above formula can be easily reacted with a suitable alkanol to yield o-benzylic cyclic phosphate and thiophosphate triesters such as 2-alkoxy-4H-1,3,2-benzodioxaphosphorin-2-sulfides and 2-oxides, which are valuable insecticides. A preferred compound of this class is 2-methoxy-4H-1,3,2-benzodioxaphosphorin-2-sulfide which is a well-known insecticide.

Examples of $R_1$ falling within the scope of the invention are methyl, ethyl, propyl, isopropyl, butyl, pentyl, hexyl, heptyl, octyl, nonyl, decyl, undecyl, dodecyl and the respective isomeric forms of these, cyclopropyl, cyclobutyl, chloromethyl, chloroethyl, chloropropyl, chlorobutyl, phenyl, benzyl, penÿlethyl, 3-chlorophenyl, 4-chlorophenyl, 3,4-dichlorophenyl, 4-bromophenyl, 4-nitrophenyl, 3,4-dinitrophenyl, 4-methylphenyl, 4-ethylphenyl, 4-propylphenyl, 4-methoxyphenyl, 4-ethoxyphenyl, 4-methylthiophenyl, or 4-ethylthiophenyl.

The new phospholane acid halides of this invention may be prepared by reacting an o-hydroxybenzyl alcohol with a phosphoryl or thiophosphoryl trihalide in the presence of an excess of alkaline earth metal oxide. The reaction may be run without resorting to the use of a solvent. When a solvent is used, almost any inert one may be used. Suitable solvents are, for example, benzene, toluene, xylenes, carbon tetrachloride, dichloromethane, diethyl ether, pentane, and the like. Heat is evolved during the reaction and the reactants ought to be mixed slowly, accompanied by thorough stirring. The temperature of the reaction mixture is preferably kept at room temperature, but reaction temperatures as low as about −20° C and as high as the boiling point of the solvent or the phosphoryl or thiophosphoryl trihalide, may be used.

The novel process of the present invention may be represented by the following equation (where M represents an alkaline earth metal):

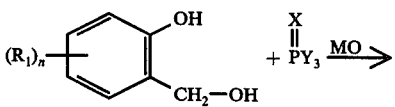

-continued

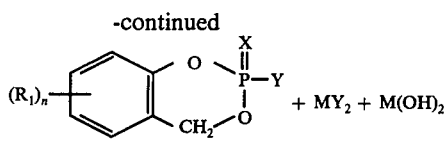

where $R_1$, X, Y and $n$ have the above meanings.

The stochiometry of the reaction calls for equimolar quantities of both reactants. However, the mole ratio of the reactants may vary from a range of 1 to 10 and 10 to 1 with no great effect on the product. A slight excess of the phosphoryl or thiophosphoryl trihalide is preferred.

Examples of the alkaline earth metal oxides are calcium oxide, barium oxide, and magnesium oxide, with calcium oxide being preferred. The purpose of the excess alkaline earth metal oxide is to react with the acid formed during the reaction and also to react with the water subsequently formed, thereby preventing the hydrolysis of the labile phosphoryl or thiophosphoryl trihalide. The metal oxides used in the present invention may be ordinary technical material, preferably in the powdered form.

The present process may be run without any catalyst. However, the presence of a small amount of an electron donor catalyst substantially increases the rate of reaction. The catalysts used in the inventive process are provided in small amounts ranging from a trace up to about 1% or more. While larger amounts of catalyst can be employed, no useful result is obtained by such a procedure. Suitable catalysts for use in the present invention include, for example, pyridine, picoline, acridine, quinoline, and the like.

The phospholane acid halides are recovered from the reaction mixture and purified by conventional methods. When the desired product separates as a solid it may be filtered off, washed to free it of by-products and of unreacted starting materials, and recrystallized from a suitable solvent such as hexane or benzene.

The novel compounds of Formula (I) above, can easily be converted to cyclic phosphorus-containing esters of Formula (II)

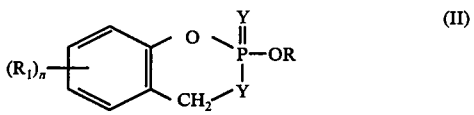

wherein R is lower alkyl of up to and including 4 carbon atoms, and wherein $R_1$, X, and $n$ have the aforedefined meanings. This reaction comprises reacting a Compound I, defined above with a lower alcohol, of up to and including 4 carbon atoms, while the hydrogen halide formed is removed.

The process of conversion of Compounds of Formula II to compounds of Formula I may be represented by the following reaction scheme:

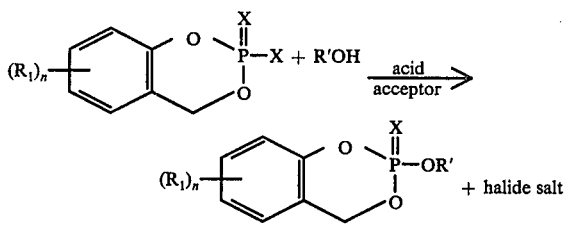

wherein R'OH designates a lower alcohol, as for example methanol, ethanol, propanol, iso-propanol, n-butanol, sec-butanol, and iso-butanol.

The acid acceptors may be mono-, di-, or tertiary amines such as ammonia, trimethylamine, triethylamine, and diphenylamine, pyridine; metal oxides such as calcium, barium, or magnesium oxide; and basic carbonates such as potassium carbonate and other alkaline bases. The hydrogen halide formed during the reaction may, alternately, be removed from the reaction mixture by bubbling through it an inert gas.

DESCRIPTION OF THE PREFERRED EMBODIMENT

The following example is illustrative of the process and products of the present invention, but is not be construed in a limitative sense.

EXAMPLE 1

Into a three-necked, 500 ml flask were placed 31 g (0.25 mole) o-hydroxybenzyl alcohol, 56 g (1.0 moles) calcium oxide, a catalytic amount (0.1 g) of acridine, and 600 ml of benzene. To this reaction mixture was added 46.5 g (0.275 mole) of thiophosphoryl trichloride, dropwise, over a period of 120 minutes with stirring. The temperature was maintained at 22° C by use of a water bath. After the addition of the thiophosphoryl trichloride the mixture was stirred overnight. The mixture was then filtered, the solids washed with four equal portions of benzene (total of 200 ml) and the washings combined with the filtrate. The filtrate was then washed with two equal portions of a 5 percent aqueous bicarbonate solution (total of 100 ml), dried over sodium sulfate, filtered, and the volatiles removed under reduced pressure. The residue crystallized, affording 39 g (71%) pf 2-chloro-4H-1,3,2-benzodioxaphosphorin-2-sulfide, m.p.=44°-45° C. Analysis: %Cl, 16.12 (calculated); 16.42 (Found).

The IR and NMR spectra were in accordance with the expected structure of the compound.

EXAMPLE 2

Into a reaction flask was placed 150 ml methanol, 21 g (0.15 moles) potassium carbonate, and 22 g (0.1 moles) of 2-chloro-4H-1,3,2-benzodioxaphosphorin-2-sulfide. The reaction mixture was stirred at room temperature for 2 hours, filtered, and the axcess methanol recovered via reduced pressure. The residue was dissolved in 50 ml chloroform, washed with two portions of water (total of 100 ml), dried over sodium sulfate, filtered, and the solvent removed under reduced pressure. The residue crystallized to yield 19.2 g (92%) of 2-methoxy-4H-1,3,2-benzodioxaphosphorin-2-sulfide having a melting point 50°-53° C. The melting point, IR and NMR spectra of this product were identical to the known insecticide, Salithion. By using corresponding alkanols instead of methanol, the corresponding 2-alkoxy derivatives are obtained.

The starting compound was obtained according to Example 1.

EXAMPLE 3

2-Chloro 4-H-1,3,2-benzodioxaphosphorin-2-sulfide was prepared according to the procedure of Example 1, but with 1 mole barium oxide instead of the calcium oxide. The same product and yield were obtained as in Example 1.

What is claimed is:

1. A process for preparing compounds of the formula

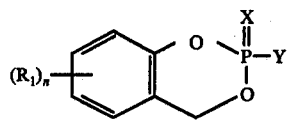

wherein
$R_1$ is selected from the group consisting of hydrogen, alkyl, alkylene having up to 12 carbon atoms, cycloalkyl, aralkyl, aryl, alkaryl, halogen, cyano, nitro, alkoxy, alkylthio, aryloxy, haloalkyl, and haloaryl;
$n$ is an integer from zero to 4;
X is oxygen or sulfur;
Y is chlorine or bromine;
which comprises
reacting an o-hydroxybenzyl alcohol with a phosphoryl or thiophosphoryl trihalide in the presence of an excess of an alkaline earth metal oxide at a temperature between $-20°$ C to the boiling point of the solvent and separating the resultant 2-halo-4H-1,3,2-benzodioxaphosphorin-2-sulfide or -2-oxide.

2. A process according to claim 1 wherein the reactants are o-hydroxybenzyl alcohol, thiophosphoryl trichloride, and calcium oxide.

3. A process according to claim 1 wherein the reactants are o-hydroxybenzyl alcohol, thiophosphoryl trichloride, and barium oxide.

4. A process according to claim 1 wherein the reactants are o-hydroxybenzyl alcohol, phosphoryl trichloride, and calcium oxide.

5. A process in accordance with claim 1 further including a catalytic quantity of electron donor catalyst.

6. A process in accordance with claim 5 wherein said electron donor catalyst is selected from the group consisting of pyridine, picoline, acridene and quinoline.

* * * * *